United States Patent
Borbely et al.

(10) Patent No.: US 7,740,883 B2
(45) Date of Patent: Jun. 22, 2010

(54) NANOPARTICLES FROM CHITOSAN

(75) Inventors: Janos Borbely, Debrecen (HU);
Magdolna Bodnar, Hajduboszormeny (HU)

(73) Assignee: University of Debrecen (HU)

( * ) Notice: Subject to any disclaimer, the term of this patent is extended or adjusted under 35 U.S.C. 154(b) by 1224 days.

(21) Appl. No.: 11/091,940

(22) Filed: Mar. 28, 2005

(65) Prior Publication Data
US 2005/0226938 A1    Oct. 13, 2005

Related U.S. Application Data

(60) Provisional application No. 60/557,257, filed on Mar. 28, 2004.

(51) Int. Cl.
*C08B 37/08* (2006.01)
(52) U.S. Cl. ............... 424/492; 424/499; 514/2; 514/44; 536/20
(58) Field of Classification Search ........... 424/492, 424/499; 514/2, 44; 536/20
See application file for complete search history.

(56) References Cited

U.S. PATENT DOCUMENTS

| 5,645,844 | A |  | 7/1997 | Henderson et al. |  |
|---|---|---|---|---|---|
| 5,824,339 | A | * | 10/1998 | Shimizu et al. | 424/466 |
| 6,228,291 | B1 |  | 5/2001 | Lee et al. |  |
| 6,252,003 | B1 | * | 6/2001 | Kuwahara et al. | 525/242 |
| 6,359,032 | B1 | * | 3/2002 | Kuwahara et al. | 523/201 |
| 6,391,318 | B1 |  | 5/2002 | Illum et al. |  |
| 6,465,626 | B1 |  | 10/2002 | Watts et al. |  |
| 6,509,039 | B1 |  | 1/2003 | Nies |  |
| 6,602,952 | B1 |  | 8/2003 | Bentley et al. |  |
| 6,638,918 | B2 |  | 10/2003 | Davison et al. |  |
| 6,750,271 | B2 | * | 6/2004 | Nanbu et al. | 523/201 |
| 7,309,500 | B2 | * | 12/2007 | Kim et al. | 424/489 |
| 2006/0052492 | A1 | * | 3/2006 | Harashina et al. | 524/100 |

* cited by examiner

*Primary Examiner*—Peter D. Mulcahy
*Assistant Examiner*—Henry Hu
(74) *Attorney, Agent, or Firm*—Thomas A. O'Rourke; Bodner & O'Rourke, LLP

(57) ABSTRACT

Methods are disclosed for preparing crosslinked core and core-shell nanoparticle polymers from chitosan. The final products of the present invention may be used as detergents and as additives for pharmaceutical composition and for drug delivery, and DNA carrier system. The nanoparticles made from biopolymers of the present invention may also be used in controlled release, superabsorbent materials and biomaterials like enzyme immobilization.

14 Claims, No Drawings

NANOPARTICLES FROM CHITOSAN

This is a conversion of United States Application Ser. No. 60/557,257 filed Mar. 28, 2004 the disclosures of which are incorporated herein by reference.

FIELD OF THE INVENTION

The present invention relates to crosslinked chitosan compositions, especially to chitosan compositions comprising nano-sized chitosan that have been amidized with carboxyl groups.

BACKGROUND OF THE INVENTION

Biomaterials made from polymers are being extensively applied in medicine and biotechnology, as well as in other industries. Applications include use as supporting materials, drug-delivery systems with different routes of administration and design, carriers of immobilized enzymes and cells, and materials for orthopedic applications.

Chitosan is a renewable biomaterial, $\beta$-[1→4]-2-amino-2-deoxy-D-glucopyranose, a functional and basic linear polysaccharide, and is prepared from chitin, the second most abundant biopolymer in nature. Chitosan is prepared by N-deacetylation of chitin, resulting in a copolymer of $\beta$-[1→4]-linked 2-acetamido-2-deoxy-D-glucopyranose and 2-amino-2-deoxy-D-glucopyranose. Chitosan is commercially available in a wide variety of molecular weight (e.g., 10-1000 kDa) and usually has a degree of deacetylation ranging between 70%-90%.

Recently there has been considerable interest in chitosan. For example, in U.S. Pat No. 5,645,844 to Henderson et, the inventor uses a negatively charged chitosan derivative delivery system which releases a semiochemical at a sustained rate over an extended period for time to attract a target insect to a selected location or to disrupt mating patterns. Watt et al., U.S. Pat. Nos. 6,465,626 and 6,391,318 uses chitosan in connection with vaccine compositions for intranasal administration. Cross-linked polymers of chitosan or alkoxy poly (alkylene oxide) conjugates of chitosan are described in U.S. Pat. No. 6,602,952 to Bentley et al. Crosslinking reactions with chitosan using sulfuric acid and glutaraldehyde are described in U.S. Pat. No. 6,228,291 to Lee et al.

Polymer emulsions comprising polymer particles having core-part and shell-part and having an average particle size of not more than 30 .mu.m, are disclosed in U.S. Pat. No. 6,359,032 to Kuwahara et al. The shell-part in Kuwahara is composed of chitosan and a polymer of an organic acid having a reactive vinyl group or a salt thereof as constituent components. The core-part is composed of a polymer of a hydrophobic monomer as constituent component or a mixture of the hydrophobic monomer and a non-polymerizable hydrophobic substance. U.S. Pat. No. 6,509,039 to Nies discloses a pharmaceutical composition comprising an active ingredient and a pharmaceutically acceptable carrier, where the carrier is a cross linked product of chitosan obtained by reacting chitosan with a carboxylic acid dianhydride or carboxylic acid polyanhydride. Compositions claimed to have pure nanoparticulate chitosan, which is free from surface modifiers or organic solvents are disclosed in U.S. Pat. No. 6,638,918 to Davison et al. The disclosures of the foregoing patents are hereby incorporated herein by reference.

The specific solubility characteristics of chitosan set limits to practical use. The only suitable aqueous media for dissolving chitosan are dilute acidic media such as hydrochloric acid, and some organic acids such as, for example, acetic acid and lactic acid. Chitosan is virtually insoluble in other media and conventional solvents. Chitosan solutions can be accordingly employed only where the aqueous acidic dissolving medium is not a problem. However, a variety of studies have focused on altering the water solubility of chitosan material in aqueous solution by employing water soluble linkages like phosphates, sulfates, cyanates and other agents.

Currently, because of its special set of properties, which include low or non-toxicity, biocompatibility, biodegradability, low immunogeneicity and antibacterial properties, chitosan has found wide application in a variety of areas, such as biomedicine, pharmaceutics, metal chelation, food additive, and other industrial utilizations.

Various methods have been developed for the crosslinking of chitosan including chemical modification of linear macromolecules with aldehydes, epoxides, cyanates and other agents, and ionically crosslinking reactions with charged ions or molecules to form bridges between polymeric chains. Crosslinking commonly results in gel formation.

Chitosan is of increasing interest in drug delivery. It is known, for example, to enhance transport of hydrophilic drugs. It has also reported to be useful in colon- or nasal delivery. Chitosan is also of current interest as a carrier in gene delivery. Several chitosan nanocomposites were evaluated based on the ionotropic gelation, or numerous chitosan/DNA nanoparticles were framed from the complexation of the cationic polymer with DNA plasmid. Ionically interaction and modification only of chitosan as cationic polymer and anions result in these particles.

SUMMARY OF THE INVENTION

The present invention relates to core-shell polymers of linear polyamines and more preferably chitosan, especially to nano-sized derivatives thereof. Precrosslinked chitosan compounds are prepared by chemical modification of chitosan with one or more mono-, di-, tri- and polycarboxylic acids or blends thereof. This resulting core could be hydrophilic, hydrophobic or amphiphilic depending on the percentage of crosslinking present and the character of carboxylic acid used. The chitosan that may be used as the as a polyamine may differ in molecular weight and in the degree of deacylation and may include blends of differing chitosan.

In the reaction with the carboxylic acid it is believed that the NH2 amine groups of the linear chitosan macromolecule react with the mono/di/tri/poly carboxylic acids to form an amide linkage and the di/tri/poly acids form an intramolecular bridge. Due to this reaction the starting coiled Chitosan structure is transformed into a globular spherical nanoparticle. In the reaction a carbodiimide CDI reacts with water eliminated during formation of amide linkage between Chitosan and the carboxylic acids.

In the preferred embodiment, the chitosan first reacts with a carboxyl compound thereby forming a partially crosslinked or modified nanoparticle. The surface of the chitosan compound so formed has a plurality of molecules on the shell. The precrosslinked chitosan nanoparticles on the surface have amine and hydroxy groups on the shell. More particularly, after amidizing the chitosan, the next step is the reaction of these precrosslinked chitosan compounds with one or more functional carboxylic acids. Functional groups of these molecules preferably contain vinyl groups. The polymerization of the vinyl groups by chemical or by UV or blue light initiation can produce a hydrophobic shell of nanoparticles or stable ions. In one embodiment, the nanoparticles have vinyl groups on the surface may take place in a polymerization reaction forming hydrogels. Hydrogels from biopolymers are described in our copending application Ser. No. 11/074,314 filed Mar. 7, 2005, the disclosures of which are incorporated herein by reference. The nanoparticles may be positively or negatively cherged, e.g., from the chitosan NH3+ cation, or from the carboxylic acid moiety, the COO— anion. The positively charge corona/shell (NH3+) of the nanoparticles will form an ion-ion interaction with oligonucleotides (DNA, RNA) which are negatively charged. The invention also relates to a process for making the compositions.

The chitosan compositions formed in accordance with the present invention are in the form of a network of nano-sized, biocompatible and biodegradable, crosslinked particles. These particles are obtained by reacting chitosan and at least one carboxylic acid having at least two carboxyl groups thereon. More preferably, the process for the preparation of the nano-sized, biocompatible and biodegradable, crosslinked particles is performed by reacting chitosan in the presence of the carboxylic acid as a crosslinking agent and a carbodiimide as an activator.

The nano-size particles formed by the reaction have an average diameter ranging from about 30 nm to about 250 nm, as determined by transmission electron microscopic imaging. In one embodiment, the carboxylic acid that is the crosslinking agent is selected from the group consisting of di-, tri-, or polycarboxylic acids. The chitosan may be a natural chitosan or a degraded chitosan such as a lipase-degraded chitosan.

Core-shell nanosystems can be formed from the reaction product of the reaction of the chitosan with the carboxylic acid having at least two carboxyl groups thereon. The shell can be made from a carboxylic acid such as a monocarboxylic acid. Preferred monocarboxylic acids are monocarbxylic acids having one or more vinyl-, benzyl-, and/or alkyl-groups. The monocarboxylic acid can also be a positively charged or a negatively charged molecule when present in an aqueous media.

DETAILED DESCRIPTION

The starting material of the present invention is a polyamine such as chitosan a derivative of natural chitin. After cellulose, chitin is the second most abundant natural biopolymer on earth. One of the derivatives of chitin is chitosan, which may be obtained by the N-deacetylation of chitin. Chitosan is a copolymer of N-acetylglucosamine and glucosamine. It is a biocompatible and biodegradable linear polyamine. A limiting factor in the modification and application of chitosan is its low solubility. Chitosan is, however, soluble in aqueous acidic media and forms a viscous solution. Chitosan and its solution have found wide variety of applications, such as in medicine, pharmaceuticals, and food technology.

In the present invention chitosan was purified by dissolution in hydrochloric acid and followed by precipitation with NaOH. The purified chitosan was washed with distilled water and freeze dried.

After freeze drying, chitosan is then partially amidated by reacting it with one or more mono-, di-, tri- or polycarboxylic acid compounds. The carboxylic acids is preferably a naturally nontoxic carboxylic acid so that the resulting product may be used in pharmaceutical applications, and other applications where toxicity may be an issue.

Preferred monocarboxylic acids are:
Aliphatic monocarboxylic acid, such as:
  n-butyric acid
  Propionic acid
Hydroxy-monocarboxylic acids, such as
  Salicylic acid
  Mandelic acid
Aromatic monocarboxylic acids, such as:
  Benzoic acid
  Phenylacetic acid
Heteroaromatic monocarboxylic acid, such as:
  Nikotinic acid
  Preferred dicarboxylic acid compound include:
Aliphatic di/tri/polycarboxylic acids, such as:
  HOOC—$(CH_2)_n$—COOH n=0 to 4
  Oxalic acid
  Malonic acid
  Succinic acid
  Glutaric acid
  Adipic acid
Hydroxi-di/tri/polycarboxylic acids, such as
  HOOC—$(CH_2)_n$—$(CHOH)_m$—COOH n=0 to 2 and m=0 to 2, such as:
  Malic acid
  Tartaric acid
  Citric acid
  2-hydroxi-maleic acid
  1,3-acetonedicarboxylic acid
  Mucic acid
Oxo-di/tri/polycarboxylic acid, such as:
  Oxalacetic acid
Aromatic di/tri/polycarboxylic acids, such as:
  Phtalic acid
  Terephtalic acid
Unsaturated di/tri/polycarboxylic acid, such as:
  Maleic acid
  Fumaric acid
  Muconic acid
Others, such as:
  Poly-(ethylenglycol)-bis-(carboxymethylether)

The reaction that is performed determines the precrosslinking of chitosan. This precrosshinking can performed so that the amounts of crosslinking in the final product can be varied as desired, i.e., from 1 to 99% crosslinking. The amidizing reaction takes place in water, in the presence of a water soluble carbodiimide (CDI) compound, which preferably is 1-[3-(dimethylamino)propyl]-3-ethylcarbodiimide hydrochloride.

The core is formed by crosslinking the chitosan or by self-assembly of the chitosan linear chain.

The partially precrosslinked products can be further vinylized. The content of vinyl groups is preferably from about 5 to about 50%, more preferably 10 to 30%, reported to the free amino groups from the precrosslinked chitosan products. Preferred water soluble carboxylic acids containing vinyl groups that may be used for vinylizing the partially precrosslinked product include but are not limited to:
  Acrylic acid
  Methacrylic acid In this second stage the outer shell of the core shell polymer is formed from hydrophobic compounds that optionally may be crosslinked a priori. The core-shell morphology may be a result of self assembly of modified chitosan in the case when hydrophobic side chains are introduced. Therefore, in aqueous solution, the hydrophobic chains are in the inner part and the residual hydrophilic segments occupy the corona. These particles are designed for solubilization of water insoluble lipophilic compounds and other compounds. Other compounds can include lipophilic vitamins, such as A, B, D, E vitamins. Cholesterol, sitosterol, ergosterol and 7-dehydrocholesterol are preferred sterols that may also be used. Vitamins and provitamins can also be used. Vitamins A, D, E, and K are preferred vitamins and provitamin A(.beta.-carotene) is a preferred provitamin. Macrolide antibiotics may also be used. Among the macrolide antibiotics that can be used, polyene antibiotics, amphotericin-B, nystatin, and candicidin are preferred. Coenzymes such as $Q_{10}$ are of particular interest. Coenzyme Q10 is a natural compound whose therapeutic potential has been recently recognized for a number of conditions and disorders related to mitochondrial dysfunctions and/or tissue damage caused by free radicals and oxidants.

The partial precrosslinked chitosan can be further amidated with different compounds if desired to obtain core-shell morphology. The content of the functional groups is preferably from about 5 to about 50%, more preferably 10 to 30% of the free amino groups from the precrosslinked chitosan products. Preferred carboxylic acids have high hydrophilic character or stable charge to form hydrophilic and/or a charged shell. Preferred carboxylic acid, include:

Poly-(ethylenglycol)-carboxylic acid

Betaine hydrocloride

The core and the outer shell can be either hydrophobic or hydrophilic. The reaction for forming the core shell polymer takes place in a multi-step process. The formation of the primary crosslinked core is followed by formation of a covalently attached shell. The reaction is controlled by the conditions of reaction (e.g., concentration, molar ratio) to obtain a very slightly crosslinked core wherein the porosity is very high, or to obtain a very highly crosslinked core wherein the porosity is very low. The degree of crosslinking could be in the range of from about 1% to about 99%.

EXAMPLE 1

Preparation of Chitosan (Solution)

Chitosan was dissolved in hydrochloric acid media, the undissolved constituents were removed by filtration. Chitosan solution was precipitated with 0.2M NaOH solution. The purified chitosan was washed with distilled water and freeze dried. The obtained chitosan was dissolved in hydrochloric acid to produce chitosan solution, concentration is 1 mg/ml. The pH was adjusted to 6.5 with NaOH.

EXAMPLE 2

Partial Crosslinking of Chitosan—Hydrophilic Core (10% of the Free Amino Groups are Reacting)

9.3 mg tartaric acid was dissolved in 50 ml of water and then neutralized to pH 6.5 with 0.1 M sodium hydroxide. After the addition 36.9 mg of water soluble carbodiimide, the reaction was stirred at 4° C. for 30 min and subsequently mixed with 200 mg chitosan (Example 1) solution at ambient temperature for 24 hours. After this time the resulting solution containing chitosan nanoparticles was purified by dialysis for 7 days against distilled water and freeze dried.

EXAMPLE 3

Partial Crosslinking of Chitosan—Hydrophilic Core (50% of the Free Amino Groups are Reacting)

46.5 mg tartaric acid was dissolved in 50 ml of water and then neutralized to pH 6.5 with 0.1 M sodium hydroxide. After the addition 184.5 mg of water soluble carbodiimide, the reaction was stirred at 4° C. for 30 min and subsequently mixed with 200 mg chitosan (Example 1) solution at ambient temperature for 24 hours. After this time the resulting solution containing chitosan nanopatricles was purified by dialysis for 7 days against distilled water and freeze dried.

EXAMPLE 4

Partial Crosslinking of Chitosan—Amphiphilic Core (50% of the Free Amino Groups are Reacting)

65.2 mg citric acid was dissolved in 50 ml of water and then neutralized to pH 6.5 with 0.1 M sodium hydroxide. After the addition 184.5 mg of water soluble carbodiimide, the reaction was stirred at 4° C. for 30 min and subsequently mixed with 200 mg chitosan (Example 1) solution at ambient temperature for 24 hours. After this time the resulting solution containing chitosan nanopatricles was purified by dialysis for 7 days against distilled water and freeze dried.

EXAMPLE 5

Partial Modification of Chitosan—Hydrophobic Core (50% of the Free Amino Groups are Reacting)

85.7 mg salicylic acid was dissolved in 50 ml of water and then neutralized to pH 6.5 with 0.1 M sodium hydroxide. After the addition 184.5 mg of water soluble carbodiimide, the reaction was stirred at 4° C. for 30 min and subsequently mixed with 200 mg chitosan (Example 1) solution at ambient temperature for 24 hours. After this time the resulting solution containing chitosan nanopatricles was purified by dialysis for 7 days against distilled water and freeze dried.

EXAMPLE 6

Partial Modification of Chitosan—Hydrophobic Core (50% of the Free Amino Groups are Reacting)

54.7 mg n-butyric acid was dissolved in 50 ml of water and then neutralized to pH 6.5 with 0.1 M sodium hydroxide. After the addition 184.5 mg of water soluble carbodiimide, the reaction was stirred at 4° C for 30 min and subsequently mixed with 200 mg chitosan (Example 1) solution at ambient temperature for 24 hours. After this time the resulting solution containing chitosan nanopatricles was purified by dialysis for 7 days against distilled water and freeze dried.

EXAMPLE 7

Reaction Between 10% Precrosslinked Chitosan and Products Which Contain Vinyl Group—Hydrophobic Shell 77.8 mg acrylic acid was dissolved in 50 ml of water and then neutralized to pH 6.5 with 0.1 M sodium hydroxide. After the addition 312.2 mg of water soluble carbodiimide, the reaction was stirred at 4° C. for 30 min and subsequently mixed with solution of 200 mg 10% precrosslinked chitosan (Example 2) solution at ambient temperature for 24 hours.

After this time the resulting solution containing core-shell chitosan nanopatricles was purified by dialysis for 7 days against distilled water and freeze dried.

EXAMPLE 8

Reaction Between 50% Precrosslinked Chitosan and Products Which Contain Water Soluble Linkage-Hydrophilic Shell 317 mg poly-(ethylenglycol)-bis-(carboxymethylether) was dissolved in 50 ml of water and then neutralized to pH 6,5 with 0.1 M sodium hydroxide. After the addition 157.2 mg of water soluble carbodiimide, the reaction was stirred at 4° C. for 30 min and subsequently mixed with solution of 200 mg 50% precrosslinked chitosan (Example 3) solution at ambient temperature for 24 hours. After this time the resulting solution containing core-shell chitosan nanopatricles was purified by dialysis for 7 days against distilled water and freeze dried.

EXAMPLE 9

Reaction Between 50% Precrosslinked Chitosan and Products Which is Charged Positively—Polyion Shell 71.7 mg betaine hydrochloride was dissolved in 50 ml of water and then neutralized to pH 6.5 with 0.1 M sodium hydroxide. After the addition 157.2 mg of water soluble carbodiimide, the reaction was stirred at 4° C. for 30 min and subsequently mixed with solution of 200 mg 50% pre-crosslinked chitosan (Example 3) solution at ambient temperature for 24 hours. After this time the resulting solution containing core-shell chitosan nanopatricles was purified by dialysis for 7 days against distilled water and freeze dried.

What is claimed is:

1. A process for forming a core shell polymer comprising forming a core by reacting one or more mono/di/tri or polycarboxylic acids or blends thereof with chitosan to form a first solution containing a chitosan nanoparticle that is partially crosslinked, wherein each of said carboxylic acids contains no vinyl group and wherein at least one of said carboxylic acids has at least two carboxyl groups thereon, said carboxyl groups forming an amide linkage between said carboxylic acid and said chitosan, and wherein said partially crosslinked nanoparticle core has a surface with one or more amino groups thereon; forming a shell on said core nanoparticle by reacting a water soluble carboxylic acid containing one or more vinyl groups with said amino groups on said surface of said partially crosslinked nanonparticle to form a second solution containing said core shell polymer, said vinyl carboxylic acid forming an amide linkage between said vinyl carboxylic acid and said amino groups on said surface of said core nanoparticle.

2. The process according to claim 1 wherein the water soluble carboxylic acid containing vinyl groups is an acrylic acid.

3. The process according to claim 1 wherein the carboxylic acid reacted with the chitosan is a nontoxic carboxylic acid.

4. The process according to claim 3 wherein the chitosan is dissolved in hydrochloric acid to produce a chitosan solution.

5. The process according to claim 4 wherein the chitosan solution is neutralized prior to the reaction with the carboxylic acid.

6. The process according to claim 1 wherein the formation of said core by reacting chitosan with a carboxylic acid takes place in water.

7. The process according to claim 1 wherein the reaction to form the core is in the presence of an activator.

8. The process according to claim 7 wherein the activator is a water soluble carbodiimide compound.

9. The process according to claim 8 wherein the water soluble carbodiimide compound is 1-[3-(dimethylamino)propyl]-3-ethylcarbodiimide hydrochloride.

10. The process according to claim 1 wherein the formation of said shell by reacting a water soluble acid containing vinyl groups with said amino groups on said surface of said partially crosslinked nanoparticle takes place in water.

11. The process according to claim 1 wherein the reaction to form the shell is in the presence of an activator.

12. The process according to claim 11 wherein the activator is a water soluble carbodiimide compound.

13. The process according to claim 12 wherein the water soluble carbodiimide compound is 1-[3-(dimethylamino)propyl]-3-ethylcarbodiimide hydrochloride.

14. The process according to claim 1 wherein the mono/di/tri or polycarboxylic acids react with said chitosan to transform said chitosan from a linear coiled macromolecule into a spherical nanoparticle.

* * * * *